(12) United States Patent
Li et al.

(10) Patent No.: US 9,062,159 B2
(45) Date of Patent: Jun. 23, 2015

(54) POLY(LACTIC-CO-GLYCOLIC ACID) SYNTHESIZED VIA COPOLYCONDENSATION CATALYZED BY BIOMASS CREATININE

(75) Inventors: Hong Li, Jiangsu (CN); Quanxing Zhang, Jiangsu (CN); Wei Jiang, Jiangsu (CN); Bingcai Pan, Jiangsu (CN)

(73) Assignee: Nanjing University, Nanjing, Jiangsu (CN)

( * ) Notice: Subject to any disclaimer, the term of this patent is extended or adjusted under 35 U.S.C. 154(b) by 0 days.

(21) Appl. No.: 14/129,111

(22) PCT Filed: Nov. 3, 2011

(86) PCT No.: PCT/CN2011/081756
§ 371 (c)(1),
(2), (4) Date: Dec. 23, 2013

(87) PCT Pub. No.: WO2013/000227
PCT Pub. Date: Jan. 3, 2013

(65) Prior Publication Data
US 2014/0142275 A1    May 22, 2014

(30) Foreign Application Priority Data
Jun. 30, 2011 (CN) .......................... 2011 1 0181169

(51) Int. Cl.
| | |
|---|---|
| *C08G 63/87* | (2006.01) |
| *A61L 27/18* | (2006.01) |
| *A61K 47/34* | (2006.01) |
| *A61L 17/00* | (2006.01) |
| *C08G 63/06* | (2006.01) |
| *C08G 63/08* | (2006.01) |
| *C08G 63/82* | (2006.01) |
| *A61L 27/54* | (2006.01) |
| *A61L 17/12* | (2006.01) |

(52) U.S. Cl.
CPC ................. *C08G 63/87* (2013.01); *A61L 27/18* (2013.01); *A61K 47/34* (2013.01); *A61L 17/00* (2013.01); *C08G 63/06* (2013.01); *C08G 63/08* (2013.01); *C08G 63/823* (2013.01); *A61L 27/54* (2013.01); *A61L 17/12* (2013.01); *A61L 2300/602* (2013.01); *A61L 2430/02* (2013.01)

(58) Field of Classification Search
CPC ....................................................... C08G 63/06
USPC ........................................................ 528/361
See application file for complete search history.

(56) References Cited

U.S. PATENT DOCUMENTS

| | | | |
|---|---|---|---|
| 4,677,191 A | 6/1987 | Tanaka | |
| 4,683,288 A * | 7/1987 | Tanaka et al. | ................. 528/361 |
| 2002/0065388 A1* | 5/2002 | Maruyama et al. | ........... 528/361 |

FOREIGN PATENT DOCUMENTS

| | | |
|---|---|---|
| CN | 1556128 | 12/2004 |
| CN | 1556128 A | 12/2004 |
| CN | 1624019 | 6/2005 |
| CN | 1624019 A | 6/2005 |
| CN | 102295765 | 12/2011 |
| CN | 102295765 A * | 12/2011 |
| WO | WO 2013000227 A1 * | 1/2013 |

OTHER PUBLICATIONS

International Search Report of PCT/CN2011/081756 dated Mar. 15, 2012.

* cited by examiner

*Primary Examiner* — Rachel Kahn
(74) *Attorney, Agent, or Firm* — Rankin, Hill & Clark LLP

(57) ABSTRACT

A method for synthesizing a medical grade biodegradable material, poly(lactic-co-glycolic acid), copolycondensation of lactic acid and glycolic acid catalyzed by biomass creatinine. The present invention uses commercialized creatinine (a type of biomaterial organic guanidine compounds—the arginine metabolite creatinine (CR) in human body) as the catalyst and industrial lactic acid (LA, mass content 85%, aqueous solution) and glycolic acid (GA, 95%) as the monomer to synthesize the high biosafety of medical poly(lactic-co-glycolic acid) in terms of two steps polycondensation without solvent. The method of the present invention has the following characters: green technology is used, raw materials required are low in costs, operation is simple and convenient, and it is easy for industrialization; the catalyst, creatinine, used in the invention has high biocompatibility and biosafety, and no cytotoxicity; the poly(lactic-co-glycolic acid) synthesized is free of any metal and other toxic residues; Further, the molecular weight distribution for all synthesized products is narrow and the molecular weight is controllable within 1.8-17.7×10$^4$; and the poly(lactic-co-glycolic acid) synthesized is suitable for use as implantable material for hard tissue repair, surgical sutures, and the carrier for targeting drugs and controlled release drugs.

2 Claims, No Drawings

POLY(LACTIC-CO-GLYCOLIC ACID) SYNTHESIZED VIA COPOLYCONDENSATION CATALYZED BY BIOMASS CREATININE

FIELD OF THE INVENTION

The invention belongs to the technical field of biodegradable medical materials, and relates to a process for synthesizing biodegradable medical polylactic-glycolic acid (lactic acid-glycolic acid copolymer) featuring a high biological safety via copolycondensation, wherein a bionic creatinine (a metabolite of arginine in human body) is used as catalyst, lactic acid and glycolic acid is used as raw materials.

BACKGROUND OF THE INVENTION

Polylactic-glycolic acid (PLGA) is an important biodegradable medical material, featuring good biocompatibility, bioabsorbability and biodegradability. Since the lactic acid-glycolic acid copolymer is formed from lactic acid and glycolic acid, it combines the advantages of two homopolymer polyester materials (polylactic acid (PLA), polyglycolic acid (PGA)). The polylactic-glycolic acid has good biocompatibility, In addition, its material strength, degradation rate, mechanical properties and the like can be modulated by changing the composition and molecular weight of the copolymer. Hence, it is a biodegradable medical material featuring a wide range of practical value. The polylactic-glycolic acid has been extensively applied in several aspects of biomedical science such as implantable hard tissue-repairing materials, surgical sutures, and the carrier for targeting drugs and controlled release drugs. It is required that the degradable materials applied in the field of biomedicine should exhibit high biological safety and not contain any toxic metal and other toxic ingredients. Currently, the production of commercially available polylactic-glycolic acid is performed via stannous octoate catalyzed ring-opening polymerization or stannous chloride catalyzed polycondensation. The recent studies throughout the world have definitely proved that divalent tin salts (stannous octoate and stannous chloride) exhibit cytotoxicity. Since the tin salt catalyst used cannot be completely removed from the synthetic polymer after polymerization reaction, the safety issue of polylactic-glycolic acid synthesized by using divalent tin-containing compound as catalyst for use as medical materials for human has been generally questioned by scientists all over the world. Thus, the exploration for efficient, non-toxic, and metal-free green catalysts for synthesizing polylactic-glycolic acid has become the challenging issue in the field of degradable biomedical materials.

SUMMARY OF THE INVENTION

The object of the present invention is to solve the safety problem which may be present in the existing polycondensation, wherein stannous chloride catalyst is used to synthesize polylactic-glycolic acid applied in the field of human medicine and pharmacy, and to provide a process for synthesizing polylactic-glycolic acid via direct copolycondensation by using a bionic creatinine as catalyst.

For the first time, the present invention develops a new process for synthesizing biodegradable medical polylactic-glycolic acid featuring a high biological safety via direct copolycondensation, wherein non-toxic, metal-free biomass creatinine (a metabolite of arginine in human body) is used as catalyst, lactic acid (LA, 85% aqueous solution) and glycolic acid (GA, 95%) are used as comonomers.

The chemical name of the non-toxic, metal-free biomass organic guanidinium compound, creatinine, as used in the present invention is 2-amino-1-methyl-2-imidazolin-4-one (the common name in English is creatinine; the abbreviation in English: CR), and the molecular structure thereof is shown as follows:

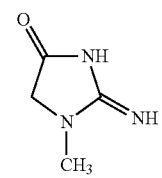

Creatinine (CR)

The process provided in the present application for synthesizing biodegradable medical polylactic-glycolic acid via direct copolycondensation of lactic acid and glycolic acid catalyzed by creatinine has the following steps:

1. The Synthesis of Oligolactic-glycolic Acid (OLGA)

Aqueous solution of industrial grade lactic acid (LA) with a mass percentage of 85% and glycolic acid (GA) with a mass percentage of 95% were used as comonomers at a molar ratio of 1:1, to firstly synthesize an oligolactic-glycolic acid (lactic acid-glycolic acid copolymer), characterized in that the weight average Mw =200~400;

Process conditions: a reactor was charged with lactic acid and glycolic acid, and then vacuumized and charged with argon for three repetitions; under an argon atmosphere at normal pressure, the reaction system was heated to 130-150° C. and subjected to dehydration for 1~3 h; the pressure in the reactor was then reduced to 100 Torr, reacting at 130~150° C. for 1~3 h; finally, the pressure in the reactor was reduced to 30 Torr, reacting at 130~150° C. for 1—3 h;

Synthetic Reaction:

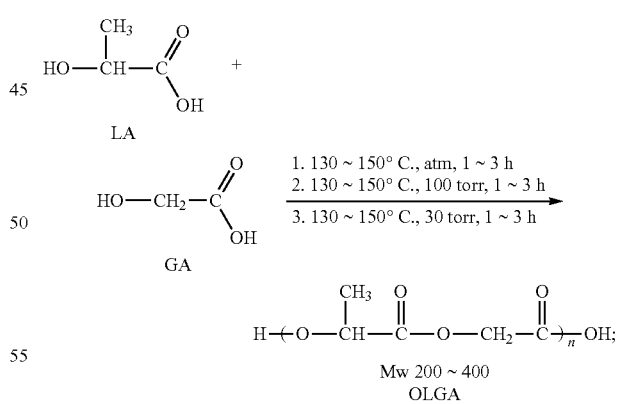

2. The Synthesis of Polylactic-glycolic Acid (PLGA)

The oligolactic-glycolic acid (LGA) synthesized in the first-step was used as raw material; the creatinine was used as catalyst; under a reduce pressure, the polycondensation of fused monomers was performed to synthesize biodegradable medical polylactic-glycolic acid featuring a high biological safety;

The process conditions and operation methods of synthetic reaction were described as follows: oligolactic-glycolic acid and creatinine catalyst were added into the reactor; the mass ratio between oligolactic-glycolic acid and creatinine was set as 100:1~1000:1; the pressure in the reactor was reduced to 10 Torr, heating to 150~190° C. for 96~170 h, to obtain polylactic-glycolic acid.
Synthetic reaction:

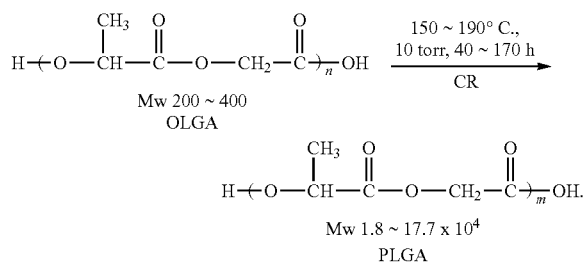

The polylactic-glycolic acid synthesized in the present invention has a weight average molecular weight within $1.8~17.7\times10^4$, and according to the actually required molecular weight, the polymer can be synthesized by controlling the time of polymerization reaction so that the molecular weight thereof falls into the above range.

The polylactic-glycolic acid synthesized according to the present application does not contain any metal and other toxic ingredients and thus can be used as implantable hard tissue-repairing materials, surgical sutures, and the carrier for targeting drugs and controlled release drugs.

The advantages and beneficial effects of the present invention are as follows:

1. The catalyst used exhibits high biocompatibility and biological safety;
2. The synthesized product exhibits high biocompatibility and biological safety and does not contain any metal and other toxic ingredients.
3. The weight average molecular weight of synthesized product, polylactic-glycolic acid, can be regulated within the range of $1.8~17.7\times10^4$;
4. The biodegradable medical polylactic-glycolic acid (featuring a high biological safety) is synthesized by using green catalyst and green process (no use of solvent, no occurrence of toxic products);
5. Low cost of raw materials, simple technical operation, easy for industrial practice.

DETAILED DESCRIPTION OF THE EMBODIMENTS

EXAMPLE 1

Synthesis of Oligolactic-glycolic Acid

A reactor was charged with 45 g of aqueous solution of industrial grade lactic acid (LA) featuring a mass percentage of 85% and 38 g of glycolic acid (GA) featuring a mass percentage of 95%, and then vacuumized and charged with argon for three repetitions. Under an argon atmosphere at normal pressure, the reaction system was then heated to 130° C. and subjected to dehydration for 3 h. The pressure in the reactor was then reduced to 100 Torr, reacting at 130° C. for 3 h, Finally, the pressure in the reactor was reduced to 30 Torr, reacting at 130° C. for 3 h, to give oligolactic-glycolic acid (OLGA) (yield: 98.0%), with a weight average molecular weight of 220.

EXAMPLE 2

Synthesis of Oligolactic-glycolic Acid

A reactor was charged with 45 g of aqueous solution of industrial grade lactic acid (LA) featuring a mass percentage of 85% and 38 g of glycolic acid (GA) featuring a mass percentage of 95%, and then vacuumized and charged with argon for three repetitions. Under an argon atmosphere at normal pressure, the reaction system was then heated to 150° C. and subjected to dehydration for 1 h. The pressure in the reactor was then reduced to 100 Torr, reacting at 150° C. for 1 h. Finally, the pressure in the reactor was reduced to 30 Torr, reacting at 150° C. for 1 h, to give oligolactic-glycolic acid (OLGA) (yield: 98.2%), with a weight average molecular weight of 280.

EXAMPLE 3

Synthesis of Oligolactic-glycolic Acid

A reactor was charged with 45 g of aqueous solution of industrial grade lactic acid (LA) featuring a mass percentage of 85% and 38 g of glycolic acid (GA) featuring a mass percentage of 95%, and then vacuumized and charged with argon for three repetitions. Under an argon atmosphere at normal pressure, the reaction system was then heated to 140° C. and subjected to dehydration for 2 h. The pressure in the reactor was then reduced to 100 Torr, reacting at 140° C. for 2 h. Finally, the pressure in the reactor was reduced to 30 Torr, reacting at 140° C. for 2 h, to give oligolactie-glycolic acid (OLGA) (yield: 98.6%), with a weight average molecular weight of 400.

EXAMPLE 4

Synthesis of Polylactic-glycolic Acid 70 g of oligoactic-glycolic acid and 265 mg of creatinine catalyst were added into the reactor. The pressure in the reactor was reduced to 10 Torr, heating to 190° C. for 40 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 85.9%), with a weight average molecular weight of $1.83\times10^4$.

EXAMPLE 5

Synthesis of Polylactic-glycolic Acid 70 g of oligoactic-glycolic acid and 265 mg of creatinine catalyst were added into the reactor. The pressure in the reactor was reduced to 10 Torr, heating to 170° C. for 48 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactie-glycolic acid (yield: 85.0%), with a weight average molecular weight of $1.86\times10^4$.

EXAMPLE 6

Synthesis of Polylactic-glycolic Acid 70 g of oligoactic-glycolic acid and 265 mg of creatinine catalyst were added into the reactor. The pressure in the reactor was reduced to 10 Torr, heating to 150° C. for 54 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 87.4%), with a weight average molecular weight of $1.80 \times 10^4$.

EXAMPLE 7

Synthesis of Polylactic-glycolic Acid 70 g of oligoactic-glycolic acid and 265 mg of creatinine catalyst were added into the reactor. The pressure in the reactor was reduced to 10 Torr, heating to 190° C. for 124 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 85.1%), with a weight average molecular weight of $7.12 \times 10^4$.

EXAMPLE 8

Synthesis of Polylactic-glycolic Acid 70 g of oligoactic-glycolic acid and 265 mg of creatinine catalyst were added into the reactor. The pressure in the reactor was reduced to 10 Torr, heating to 170° C. for 132 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 85.6%), with a weight average molecular weight of $7.08 \times 10^4$.

EXAMPLE 9

Synthesis of Polylactic-glycolic Acid 70 g of oligoactic-glycolic acid and 265 mg of creatinine catalyst were added into the reactor. The pressure in the reactor was reduced to 10 Torr, heating to 150° C. for 150 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 86.2%), with a weight average molecular weight of $7.07 \times 10^4$.

EXAMPLE 10

Synthesis of Polylactic-glycolic Acid 70 g of oligoactic-glycolic acid and 265 mg of creatinine catalyst were added into the reactor. The pressure in the reactor was reduced to 10 Torr, heating to 190° C. for 154 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 84.7%), with a weight average molecular weight of $17.7 \times 10^4$.

EXAMPLE 11

Synthesis of Polylactic-glycolic Acid 70 g of oligoactic-glycolic acid and 265 mg of creatinine catalyst were added into the reactor. The pressure in the reactor was reduced to 10 Torr, heating to 170° C. for 160 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 84.5%), with a weight average molecular weight of $17.3 \times 10^4$.

EXAMPLE 12

Synthesis of Polylactic-glycolic Acid 70 g of oligoactic-glycolic acid and 265 mg of creatinine catalyst were added into the reactor. The pressure in the reactor was reduced to 10 Torr, heating to 150'C for 169 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 84.9%), with a weight average molecular weight of $17.0 \times 10^4$.

EXAMPLE 13

Synthesis of Oligolactic-glycolic Acid

A reactor was charged with 90 g of aqueous solution of industrial grade lactic acid (LA) featuring a mass percentage of 85% and 7.6 g of glycolic acid (GA) featuring a mass percentage of 95%, and then vacuumized and charged with argon for three repetitions. Under an argon atmosphere at normal pressure, the reaction system was then heated to 130° C. and subjected to dehydration for 3 h. The pressure in the reactor was then reduced to 100 Torr, reacting at 130° C. for 3 h. Finally, the pressure in the reactor was reduced to 30 Torr, reacting at 130° C. for 3 h, to give oligolactic-glycolic acid (OLGA) (yield: 98.1%), with a weight average molecular weight of 220.

EXAMPLE 14

Synthesis of Oligolactic-glycolic Acid

A reactor was charged with 15 g of aqueous solution of industrial grade lactic acid (LA) featuring a mass percentage of 85% and 102 g of glycolic acid (GA) featuring a mass percentage of 95%, and then vacuumized and charged with argon for three repetitions. Under an argon atmosphere at normal pressure, the reaction system was then heated to 130° C. and subjected to dehydration for 3 h. The pressure in the reactor was then reduced to 100 Torr, reacting at 130° C. for 3 h. Finally, the pressure in the reactor was reduced to 30 Torr, reacting at 130° C. for 3 h, to give oligolactic-glycolic acid (OLGA) (yield: 98.0%), with a weight average molecular weight of 220.

EXAMPLE 15

Synthesis of Polylactic-glycolic Acid 70 g of oligoactic-glycolic acid and 700 mg of creatinine catalyst were added into the reactor. The pressure in the reactor was reduced to 10 Torr, heating to 160° C. for 170 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 84.7%), with a weight average molecular weight of $17.1 \times 10^4$.

EXAMPLE 16

Synthesis of Polylactic-glycolic Acid 70 g of oligoactic-glycolic acid and 140 mg of creatinine catalyst were added into the reactor. The pressure in the reactor was reduced to 10 Torr, heating to 170° C. for 60 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 84.6%), with a weight average molecular weight of $1.88 \times 10^4$.

EXAMPLE 17

Synthesis of Polylactic-glycolic Acid 70 g of oligoactic-glycolic acid and 70 mg of creatinine catalyst were added into the reactor. The pressure in the reactor was reduced to 10 Torr, heating to 180° C. for 48 h. After stopping the reaction, the reactor was cooled to room temperature. The polymer was dissolved in acetone, and then poured into ethanol at 0° C., filtered at reduced pressure. The resulting product was dried under vacuum at 50° C. for 36 h, to give a white solid, i.e. polylactic-glycolic acid (yield: 85.1%), with a weight average molecular weight of $1.98 \times 10^4$.

What is claimed is:

1. A method of making polylactic-glycolic acid (PLGA) that is free of tin salt catalysts, the method comprising: reacting lactic acid (LA, 85 mass percent aqueous solution) and glycolic acid (GA, 95 mass percent), at a molar ratio of 1:1, in a two-step copolycondensation reaction as represented by the following chemical equation,

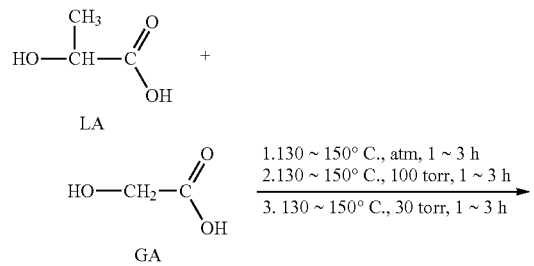

the copolycondensation reaction comprising:
  i) heating the lactic acid and the glycolic acid from about 130 ° C. to about 150 ° C. for about 1 hour to about 3 hours, in an argon atmosphere at normal pressure,
  ii) heating the lactic acid and the glycolic acid from about 130 ° C. to about 150 ° C. for about 1 hour to about 3 hours, in an argon atmosphere at a pressure of about 100 Torr, and
  iii) heating the lactic acid and the glycolic acid from about 130 ° C. to about 150 ° C. for about 1 hours to about 3 hours, in an argon atmosphere at a pressure of about 30 Torr, to thereby make oligolactic-glycolic acid (OLGA) having a weight average molecular weight of from about 200 to about 400; and reacting the oligolactic-glycolic acid (OLGA) and creatinine (CR) in a mass ratio between oligolactic-glycolic acid (OLGA) and creatinine (CR) of about 264:1, in a polycondensation reaction represented by the following chemical equation, the polycondensation reaction comprising heating the oligolactic-glycolic acid and creatinine from about 150 ° C. to about 190 ° C. for about 40 hours to about 170 hours, at a pressure of about 10 Torr to thereby make the polylactic-glycolic acid (PLGA) having a molecular weight of $1.8{\sim}17.7 \times 10^4$ that is free of tin salt catalysts.

2. The method of claim 1, wherein the polycondensation reaction of the oligolactic-glycolic acid (OLGA) and creatinine (CR) is performed for about 96 hours to about 170 hours.

* * * * *